United States Patent
Zhao et al.

(10) Patent No.: US 9,176,072 B2
(45) Date of Patent: Nov. 3, 2015

(54) DARK FIELD INSPECTION SYSTEM WITH RING ILLUMINATION

(75) Inventors: Guoheng Zhao, Milpitas, CA (US); Mehdi Vaez-Iravani, Los Gatos, CA (US); Scott Young, Soquel, CA (US); Kris Bhaskar, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 287 days.

(21) Appl. No.: 12/919,760

(22) PCT Filed: Jul. 16, 2010

(86) PCT No.: PCT/US2010/042354
§ 371 (c)(1),
(2), (4) Date: Aug. 26, 2010

(87) PCT Pub. No.: WO2011/011291
PCT Pub. Date: Jan. 27, 2011

(65) Prior Publication Data
US 2011/0169944 A1     Jul. 14, 2011

Related U.S. Application Data

(60) Provisional application No. 61/227,713, filed on Jul. 22, 2009.

(51) Int. Cl.
*H04N 7/18* (2006.01)
*G01N 21/95* (2006.01)
*G01N 21/88* (2006.01)

(52) U.S. Cl.
CPC ........ *G01N 21/9501* (2013.01); *G01N 21/8806* (2013.01); *G01N 2021/8822* (2013.01)

(58) Field of Classification Search
None
See application file for complete search history.

(56) References Cited

U.S. PATENT DOCUMENTS

| | | | |
|---|---|---|---|
| 4,740,079 A | 4/1988 | Koizumi et al. | |
| 5,953,130 A * | 9/1999 | Benedict et al. | 356/429 |

(Continued)

FOREIGN PATENT DOCUMENTS

| | | |
|---|---|---|
| CN | 1424576 A | 6/2003 |
| CN | 1685220 A | 10/2005 |

(Continued)

OTHER PUBLICATIONS

Trisnadi, Jahja. "Speckle Contrast Reduction in Laser Projection Displays". (2002) Projection Displays VIII. Proc. of SPIE vol. 4657.*

(Continued)

*Primary Examiner* — Sath V Perungavoor
*Assistant Examiner* — Dakshesh Parikh
(74) *Attorney, Agent, or Firm* — Bever, Hoffman & Harms, LLP

(57) ABSTRACT

A dark field inspection system that minimizes the speckle noise due to sample surface roughness can include a plurality of beam shaping paths for generating a composite, focused illumination line on a wafer. Each beam shaping path can illuminate the wafer at an oblique angle. The plurality of beam shaping paths can form a ring illumination. This ring illumination can reduce the speckle effect, thereby improving SNR. An objective lens can capture scattered light from the wafer and an imaging sensor can receive an output of the objective lens. Because the wafer illumination occurs at oblique angles, the objective lens can have a high NA, thereby improving optical resolution of the imaging sensor, and the resulting signal level.

30 Claims, 12 Drawing Sheets

(56) References Cited

U.S. PATENT DOCUMENTS

| | | | |
|---|---|---|---|
| 6,133,576 A | 10/2000 | Shafer et al. | |
| 6,392,793 B1 * | 5/2002 | Chuang et al. | 359/364 |
| 6,532,064 B1 * | 3/2003 | Hearn et al. | 356/237.1 |
| 7,106,432 B1 * | 9/2006 | Mapoles et al. | 356/237.2 |
| 7,227,984 B2 | 6/2007 | Cavan | |
| 7,339,661 B2 * | 3/2008 | Korngut et al. | 356/237.2 |
| 7,365,834 B2 * | 4/2008 | Lewis et al. | 356/237.2 |
| 7,454,052 B2 * | 11/2008 | Smilansky et al. | 382/149 |
| 7,630,069 B2 * | 12/2009 | Naftali et al. | 356/237.2 |
| 7,679,735 B2 * | 3/2010 | Lewis et al. | 356/237.2 |
| 7,728,966 B2 * | 6/2010 | Kim et al. | 356/237.2 |
| 7,768,635 B2 * | 8/2010 | Nakano et al. | 356/237.2 |
| 7,859,656 B2 * | 12/2010 | Uto et al. | 356/237.2 |
| 7,986,412 B2 * | 7/2011 | Jeong | 356/450 |
| 8,289,509 B2 * | 10/2012 | Wenz | 356/237.5 |
| 2003/0112432 A1 * | 6/2003 | Yguerabide et al. | 356/317 |
| 2003/0210393 A1 | 11/2003 | Vaez-Iravani et al. | |
| 2004/0095573 A1 | 5/2004 | Tsai et al. | |
| 2004/0156539 A1 * | 8/2004 | Jansson et al. | 382/145 |
| 2005/0094136 A1 | 5/2005 | Xu et al. | |
| 2005/0168729 A1 * | 8/2005 | Jung et al. | 356/237.2 |
| 2005/0219518 A1 * | 10/2005 | Korngut et al. | 356/237.2 |
| 2006/0163503 A1 | 7/2006 | Urano et al. | |
| 2006/0256327 A1 * | 11/2006 | Vaez-Iravani et al. | 356/237.2 |
| 2007/0008519 A1 | 1/2007 | Naftali et al. | |
| 2007/0177136 A1 * | 8/2007 | Nakano et al. | 356/237.2 |
| 2007/0182958 A1 * | 8/2007 | Manabe et al. | 356/237.2 |
| 2007/0206184 A1 * | 9/2007 | Uto et al. | 356/237.2 |
| 2008/0297786 A1 * | 12/2008 | Fukushima et al. | 356/244 |

FOREIGN PATENT DOCUMENTS

| | | | |
|---|---|---|---|
| JP | 56-30630 A | | 3/1981 |
| JP | 61-104243 | | 5/1986 |
| JP | 04-032067 | | 3/1992 |
| JP | H6-82376 A | | 3/1994 |
| JP | 08210989 A | * | 8/1996 |
| JP | 2005-517906 A | | 6/2005 |
| JP | 2005-214978 A | | 8/2005 |
| JP | 2006-501469 | | 1/2006 |
| JP | 2006-201044 | | 8/2006 |
| JP | 2007-517230 | | 6/2007 |
| JP | 2007-192759 A | | 8/2007 |
| JP | 2007-240512 A | | 9/2007 |
| JP | 2007232555 A | * | 9/2007 |
| JP | 2008-46075 A | | 2/2008 |
| WO | 03/069263 A2 | | 8/2003 |
| WO | 2004/031753 | | 4/2004 |
| WO | 2005/065246 | | 7/2005 |

OTHER PUBLICATIONS

Pfleegor et al. "Interference of Independent Photon Beams". (Jul. 1967) Physical Review Letters, vol. 159, No. 5.*

Mattheyses et al. "Effective Elimination of Laser Interference Fringing in Fluorescence Microscopy by Spinning Azimuthal Incidence Angle" (2006) Microscopy Research and Technique, vol. 69: p. 642-647.*

* cited by examiner

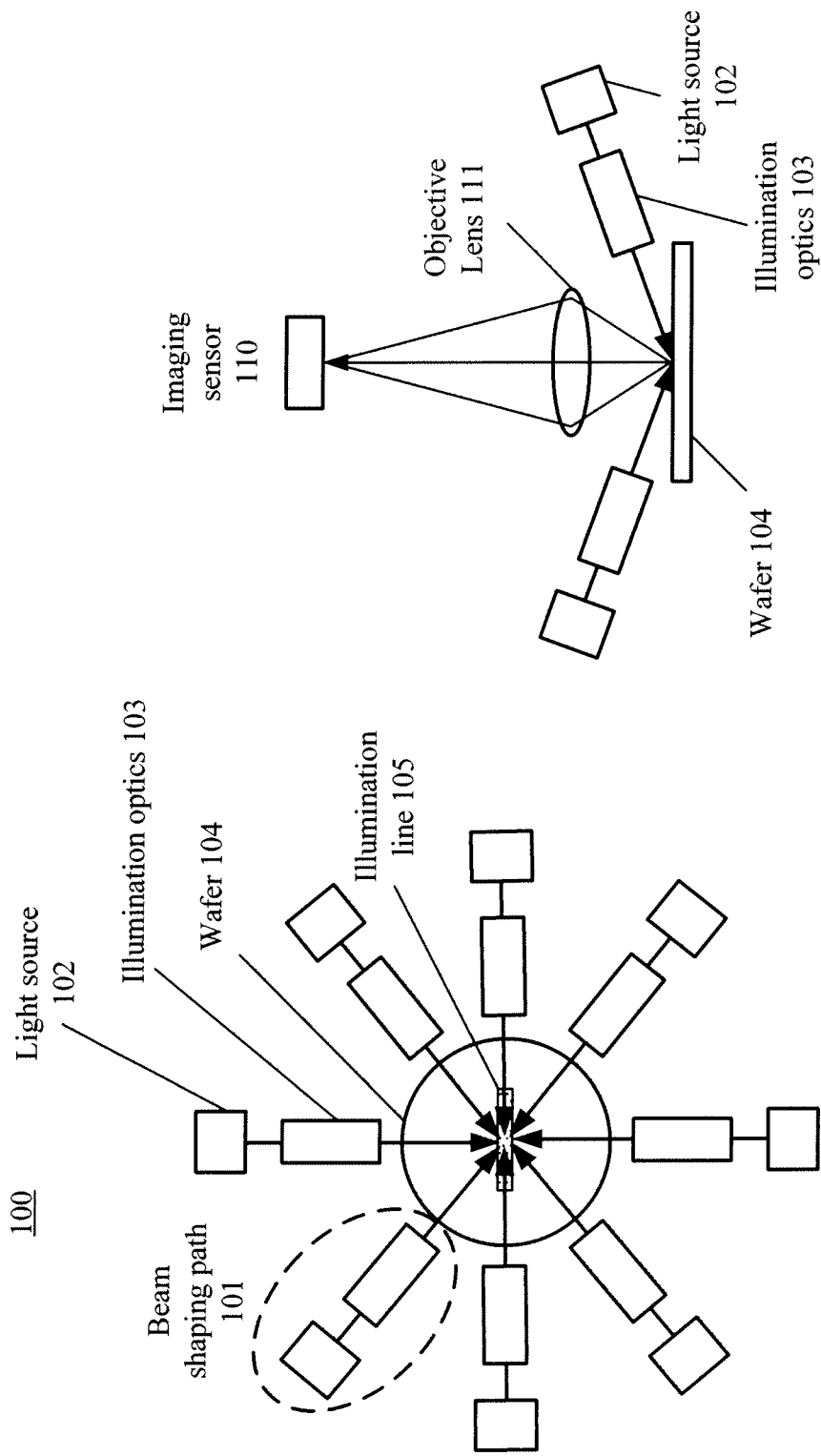

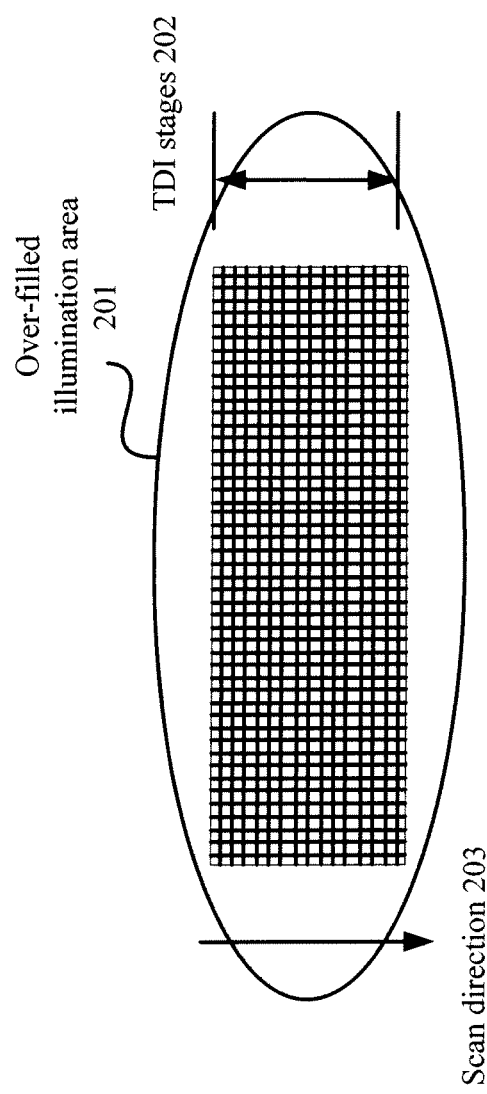
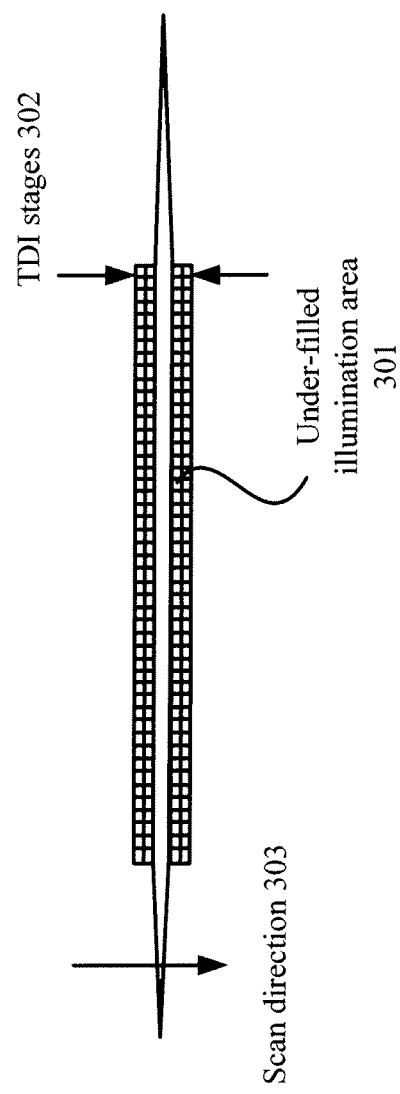

DARK FIELD INSPECTION SYSTEM WITH RING ILLUMINATION

RELATED APPLICATIONS

This application claims priority of U.S. Provisional Patent Application 61/227,713, entitled "Defect Inspection System With Enhanced Capabilities" filed Jul. 22, 2009 and PCT Application PCT/US10/42354, entitled "Dark Field Inspection System With Ring Illumination" filed Jul. 16, 2010.

BACKGROUND OF THE INVENTION

1. Field of the Invention

The present invention relates to a dark field inspection system and in particular to forming a ring illumination for this inspection system.

2. Related Art

The surface on a semiconductor wafer is optimally flat. However, even for a blank wafer, some residual roughness is inevitably present. This roughness, which may be only 2 nm or less (i.e. much less than the wavelength of light used for inspection), can still result in undesirable fluctuations in detected scattered light at an imaging sensor in a dark field inspection system. These fluctuations can be characterized as a noise floor and are referenced herein as "speckle". For wafer inspection, the speckle is effectively the limiting factor of sensitivity of the imaging sensor. That is, small particles (e.g. defects) that might otherwise be detected may be obfuscated by speckle.

Conventional methods of dark field wafer inspection have not been devised to overcome speckle, including edge contrast (EC) modes of broadband systems or laser dark field inspection systems. Unfortunately, an EC mode of a broadband system uses a low brightness broadband light source, which results in a lower illumination level at the imaging sensor. Moreover, an EC mode of the broadband system has an inherently limited numerical aperture (NA) available for defect detection because the NA is used for both illumination and imaging. This limited NA can result in low optical resolution, and relatively low collection efficiency for the scattered light.

A typical laser dark field inspection system, such as the Puma family of products offered by KLA-Tencor, uses oblique light incidence, which creates a relatively large line width (e.g. on the order of 1 um) which can somewhat limit the resolution. Moreover, a typical laser dark field inspection system uses a single angle of illumination, which results in strong spatial coherence. Strong spatial coherence can result in a relatively large level of roughness induced fluctuations (or speckle), which can affect the ultimate sensitivity of the system to real defects.

Therefore, a need arises for a dark field inspection system that can significantly improve defect detection sensitivity.

SUMMARY OF THE INVENTION

The surface roughness of a wafer typically results in small fluctuations in detected scattered light at an imaging sensor in a dark field inspection system. These fluctuations, called speckle, can be characterized as a noise floor. For wafer inspection, small defects (e.g. particles) that might otherwise be detected may be obfuscated by speckle.

A dark field inspection system that minimizes the speckle effect can include a plurality of beam shaping paths for generating a composite, focused illumination line or two-dimensional field on a wafer. Each beam shaping path can advantageously illuminate the wafer at an oblique angle. The plurality of beam shaping paths can form a ring illumination. This ring illumination can reduce the speckle effect, thereby improving SNR (signal to noise ratio). The inspection system can further include an objective lens for capturing scattered light from the wafer and an imaging sensor for receiving an output of the objective lens. Because the wafer illumination occurs at oblique angles, the objective lens can have a high NA (numerical aperture) (e.g. at least 0.5), thereby improving optical resolution. In one embodiment, the oblique angles can be between 60-85 degrees with respect to the surface normal.

In one embodiment, each of the beam shaping paths can include a light source (e.g. a laser or a laser diode) and a cylindrical lens. Each cylindrical lens can be tilted and rotated with respect to a light beam from its corresponding light source. Each cylindrical lens can have a cylindrical axis positioned parallel to the illumination line. In one embodiment, each cylindrical lens can be rotated by its cylindrical axis to minimize aberration.

In one embodiment, at least one beam shaping path includes first, second, and third cylindrical lenses. One of the first and second cylindrical lenses is in the beam shaping path at any point in time. Each of the first and second cylindrical lenses can determine a length of the illumination line. The third cylindrical lens can determine a width of the illumination line. In another embodiment, the first and second cylindrical lenses can be replaced by a zoom lens, which allows selection of a specific illumination line length within a predetermined range.

In one embodiment, the imaging sensor of the dark field inspection system can include a digital image processing filter that matches a shape of the image of a particle on the wafer. For example, the shape can be a donut shape.

In one embodiment, the plurality of beam shaping paths can include multiple lasers and multi-mode fibers coupled to the multiple lasers. A modulator can modulate beams carried by the multi-mode fibers. Mirrors can be positioned for reflecting and directing the beams for generating the illumination line. In one embodiment, the mirrors can include an aspheric ring mirror.

In another embodiment, the plurality of beam shaping paths can include a broadband light source and a light pipe for receiving an output of the broadband light source. A condenser lens can collimate the output of the light pipe. Mirrors can be positioned for reflecting and directing beams output from the condenser lens for generating the illumination line. In one embodiment, the mirrors can include an aspheric ring mirror.

In one embodiment in which each beam forming path includes a light source, at least one light source includes multiple lasers and dichroic beam combiners for generating a laser beam having multiple wavelengths. These multiple wavelengths can facilitate defect detection and identification because different defects can respond differently to different wavelengths. In another embodiment in which each beam forming path includes a light source, each light source can be a laser, and adjacent beam shaping paths have lasers with different wavelengths.

In one embodiment, the plurality of beam shaping paths can include a laser and a diffuser coupled to the laser. A fiber bundle can receive an output of the diffuser. Each fiber of the fiber bundle can contribute light to form the illumination line.

In one embodiment, the dark field inspection system can include a beam splitter positioned to receive an output of the objective lens. In this case, the imaging sensor can include multiple imaging sensors, each imaging sensor for detecting a specific wavelength of light output by the beam splitter. For example, the imaging sensor can include a first imaging sensor for detecting a first wavelength of light output by the beam splitter and a second imaging sensor for detecting a second wavelength of light output by the beam splitter. In one embodiment having three or more wavelengths output by the beam splitter, only a subset of the multiple imaging sensors may be selected for image analysis.

A method of configuring a dark field inspection system is also described. In this method, beam shaping paths to provide ring illumination are formed. Each beam shaping path is for illuminating a wafer at an oblique angle. Notably, the outputs of the plurality of beam shaping paths can form a focused illumination line on the wafer.

BRIEF DESCRIPTION OF THE FIGURES

FIG. 1A illustrates an exemplary illumination ring including a plurality of beam shaping paths, each beam shaping path including a light source and corresponding illumination optics.

FIG. 1B illustrates that the illumination ring of FIG. 1A can illuminate a wafer at oblique angles.

FIG. 2 illustrates an over-filled illumination area that can be scanned using a plurality of TDI stages in a scan direction.

FIG. 3 illustrates an under-filled illumination area that can be scanned using a substantially reduced number of TDI stages compared to the configuration shown in FIG. 2.

DETAILED DESCRIPTION OF THE FIGURES

Figure 4:
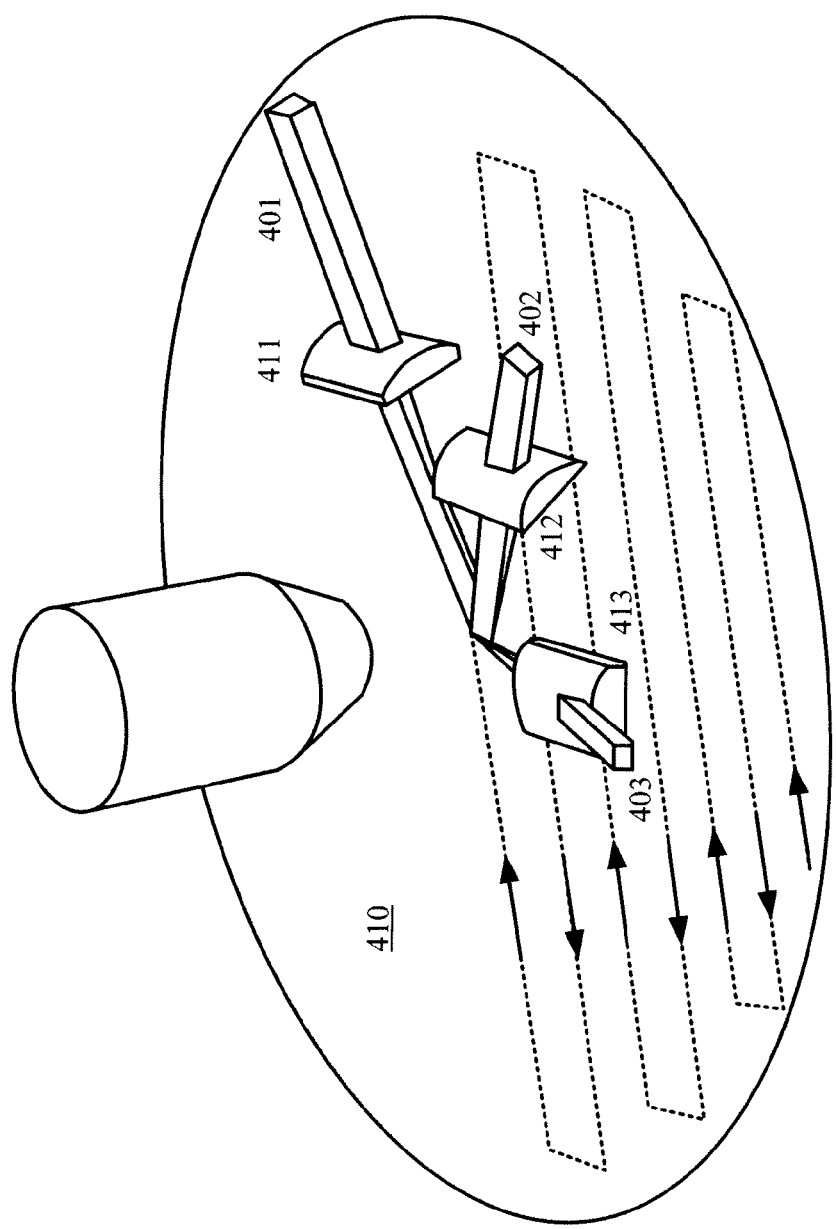
FIG. 4 illustrates an exemplary illumination configuration including three cylindrical lenses that are tilted and rotated with respect to their light beams to form a composite illuminated field on the wafer.

Roughness of a wafer's surface can result in undesirable fluctuations in detected scattered light at an imaging sensor in a dark field inspection system. For wafer inspection, this fluctuation (hereinafter called speckle) is effectively the limiting factor of sensitivity of the imaging sensor. In accordance with one aspect of an improved dark field inspection system, speckle can be reduced by using ring illumination, which can advantageously reduce the spatial coherence and thus improve optical sensitivity.

FIG. 1A illustrates an exemplary illumination ring 100 including a plurality of beam shaping paths 101. Each beam shaping path 101 can include a light source 102 and corresponding illumination optics 103. In one embodiment, light source 102 can be a laser or a laser diode. Notably, referring also to FIG. 1B, light sources 102 (via illumination optics 103) can illuminate a wafer 104 at oblique angles. In one embodiment, oblique illumination angles (as measured from wafer normal) can be from 60 to 85 degrees. These oblique illumination angles can free an objective lens 111 for imaging only, thereby allowing a high NA (e.g. from 0.5 to 0.97) to be used. An imaging sensor 110 can be positioned to receive the sample/defect scattered component of the focused light from objective lens 111 using a standard imaging path configuration (not shown for simplicity).

Notably, when two independent, random noise sources are averaged, the overall random noise decreases by $\sqrt{2}$. For N independent, random noise sources averaged, the overall random noise decreases by $\sqrt{N}$. The above-described ring illumination can provide statistically independent noise sources, i.e. speckle, thereby effectively cancelling out some noise sources while enhancing particle signal, as described in further detail below. This cancellation process is also called "averaging" herein. Note that N can be an even or odd number.

Using the above-described illumination configuration, wafer 104 can even be inspected by a broadband wafer inspection tool using time-delay integration (TDI). Various TDI techniques and configurations are described in U.S. Pat. No. 7,227,984, entitled "Method And Apparatus For Identifying Defects In A Substrate Surface By Using Dithering To Reconstruct Under-Sampled Images", issued on Jun. 5, 2007 to KLA-Tencor Corporation, and incorporated by reference herein. Note that in a broadband tool, a TDI with large number of integration stages would typically be needed to improve a light budget. For example, FIG. 2 illustrates an over-filled illumination area 203 (typical in a broadband tool) that can be scanned using TDI stages 202 in a scan direction 203. However, a TDI sensor configured with TDI stages 202 to substantially cover over-filled illumination area 201 can be expensive and difficult to produce due to the lower yield associated with the large sensor area.

Notably, light sources 102 and their corresponding illumination optics 103 can generate a thin, bright illuminated line (e.g. on the order of 10 um) on wafer 104, thereby significantly increasing the light density per unit area (compared to a broadband light source). To minimize the TDI stages, the illuminated line can be formed perpendicular to the TDI integration direction. For example, FIG. 3 illustrates an under-filled illumination area 303 (i.e. the illuminated line on the wafer) that can be scanned using a substantially reduced number of TDI stages 302 in a scan direction 303. The term "under-filled" refers to the significantly smaller area provided for illumination, in contrast to an "over-filled" illumination area (see, e.g. FIG. 2). This TDI stage reduction can significantly reduce the cost associated with the sensors while providing enough illumination brightness that is required for high sensitivity and high throughput inspection. In one embodiment, to optimize the throughput of wafer inspection, the length of the illuminated line can be in the range of 1-3 mm.

In one embodiment, for multiple azimuthal illumination angles, the illuminated lines from the different illumination angles can be at least partially superimposed to form the illuminated line, i.e. under-filled illumination area 301. In another embodiment, the illuminated lines from the different illumination angles can be effectively concatenated to form the illuminated line.

FIG. 4 illustrates an exemplary illumination configuration including three cylindrical lenses that are tilted and rotated with respect to their light beams to form a composite illuminated line on the wafer. Specifically, three cylindrical lenses 411, 412, and 413 (which would form part of the illumination optics from three beam shaping paths) can be tilted and rotated with respect to laser beams 401, 402, and 403, respectively (which would be output by their respective light sources, not shown for simplicity) to form an illuminated line on wafer 410. In one embodiment, the tilt and rotation angle can be determined by the illumination angle.

FIG. 4 shows exemplary angles of 0, 45, and 90 degree azimuth angles for cylindrical lenses 413, 412, and 413, respectively. Note that each cylindrical lens receives collimated light from its associated laser beam and generates a focused line on wafer 410 that is parallel to its long axis, which is called an a-axis.

Figure 5:
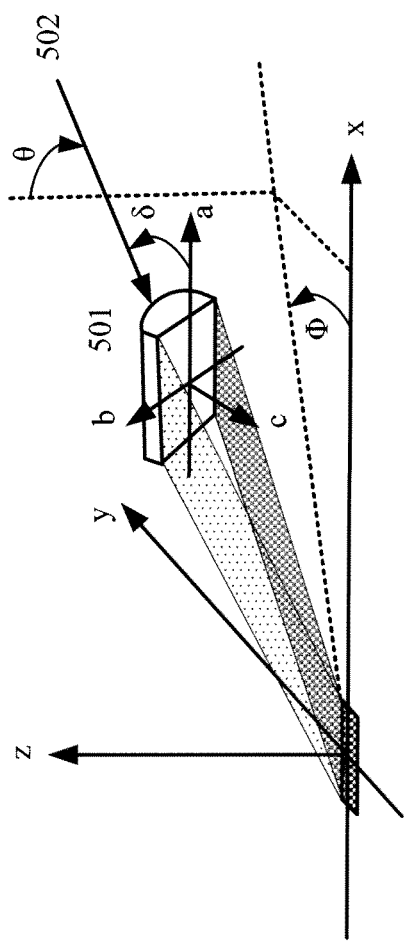

A cylindrical lens can have different orientations depending on the azimuthal angle of illumination. For example, FIG. 5 illustrates how the orientation of a cylindrical lens 501 for illuminated line generation can be determined based on the azimuthal angle $\Phi$ and the polar angle $\theta$. The a-axis is called the cylinder axis, where the c-axis is called the optical axis of the cylindrical lens. The b-axis is perpendicular to both the a-axis and the c-axis. If the line of illumination is along the x axis, then the a-axis of cylindrical lens 501 is parallel to the x-axis. In one embodiment, the b-axis of cylindrical lens 501 can be positioned perpendicular to an incident beam 502 to minimize aberration.

Because the a-axis of cylindrical lens 501 is parallel to the x-axis regardless of incident angles of illumination, the orientation of cylindrical lens 501 can be conveniently defined by the angle of rotation with respect to the a-axis. The following equations derive the orientation for a cylindrical lens as a function of the azimuthal angle $\Phi$ and the polar angle $\theta$.

The illumination beam vector can be represented by:

$$\vec{l} = \sin\theta\cos\Phi\vec{x} + \sin\theta\cos\Phi\vec{y} + \cos\theta\vec{z}$$

The cylindrical lens axis vector $\vec{a} = \vec{x}$.
The direction of b can be computed as follows:

$$\vec{b} = \frac{\vec{a} \times \vec{l}}{\sin\delta}$$

where $\delta$ is the angle between cylindrical lens $\vec{a}$ and incident beam $\vec{l}$, and is given by:

$$\cos\delta = \vec{a} \cdot \vec{l}$$
$$= \sin\theta\cos\Phi$$

Therefore, $$\vec{b} = \frac{\sin\theta\cos\Phi}{\sqrt{1-\sin^2\theta\cos^2\Phi}}\vec{z} - \frac{\cos\theta}{\sqrt{1-\sin^2\theta\cos^2\Phi}}\vec{y}$$

Note that one special case is when $\Phi=0°$: $\vec{b} = -\vec{y}$ where $\vec{b}$ is parallel to y axis. That is, the optical axis is parallel to z axis. The angle between the cylindrical lens and incident beam is 90°−θ, which is the case of an illumination arrangement for a laser dark-field inspection tool.

Another special case is when $\Phi=90°$: $\vec{b}=\sin\theta\vec{z}-\cos\theta\vec{y}$ where the cylindrical lens is perpendicular to the incident beam ($\delta=0$) which is a conventional use of cylindrical lens for focusing a laser beam.

For the purpose of aligning the cylindrical lens for focusing a laser beam at an arbitrary illumination angle, the following two steps can be used:

Step 1) align the cylindrical axis a to be parallel to the line direction (the x axis in this example), and the optical axis $\vec{c}$ parallel to the z axis; and Step 2) rotate the cylindrical lens around its cylindrical axis $\vec{a}$ by angle of $\omega$, which is given by:

$$\cos\omega = \frac{\cos\theta}{\sqrt{1-\sin^2\theta\cos^2\Phi}}$$

Figure 6:
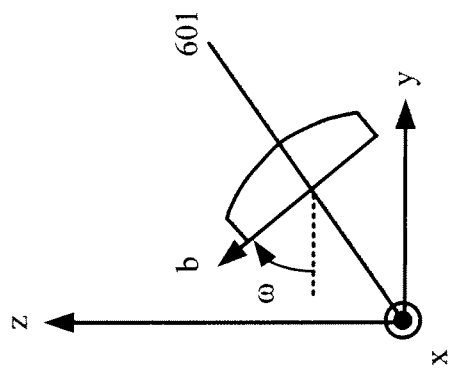
FIGS. 5 and 6 illustrate how the orientation of a cylindrical lens for illuminated field generation can be determined based on the azimuthal angle and the polar angle.

The rotation of the cylindrical lens brings the $\vec{b}$ axis of the cylindrical lens to be perpendicular to the incident beam 601, as shown in FIG. 6.

Note that step 2) can minimize aberration. Therefore, if the illumination line does not need to be tightly focused, step 2 may not be necessary.

Table 1 below lists examples of the lens rotation angles (in degrees) for various azimuth angles off illumination at a 65 degree polar incident angle.

TABLE 1

| $\Phi$ | $\omega$ | $\delta$ |
|---|---|---|
| 0 | 00.00 | 25.00 |
| 15 | 29.03 | 28.90 |
| 30 | 47.00 | 38.29 |
| 45 | 56.60 | 50.14 |
| 60 | 61.70 | 63.05 |
| 75 | 64.23 | 76.43 |
| 90 | 65.00 | 90.00 |

Figure 7:
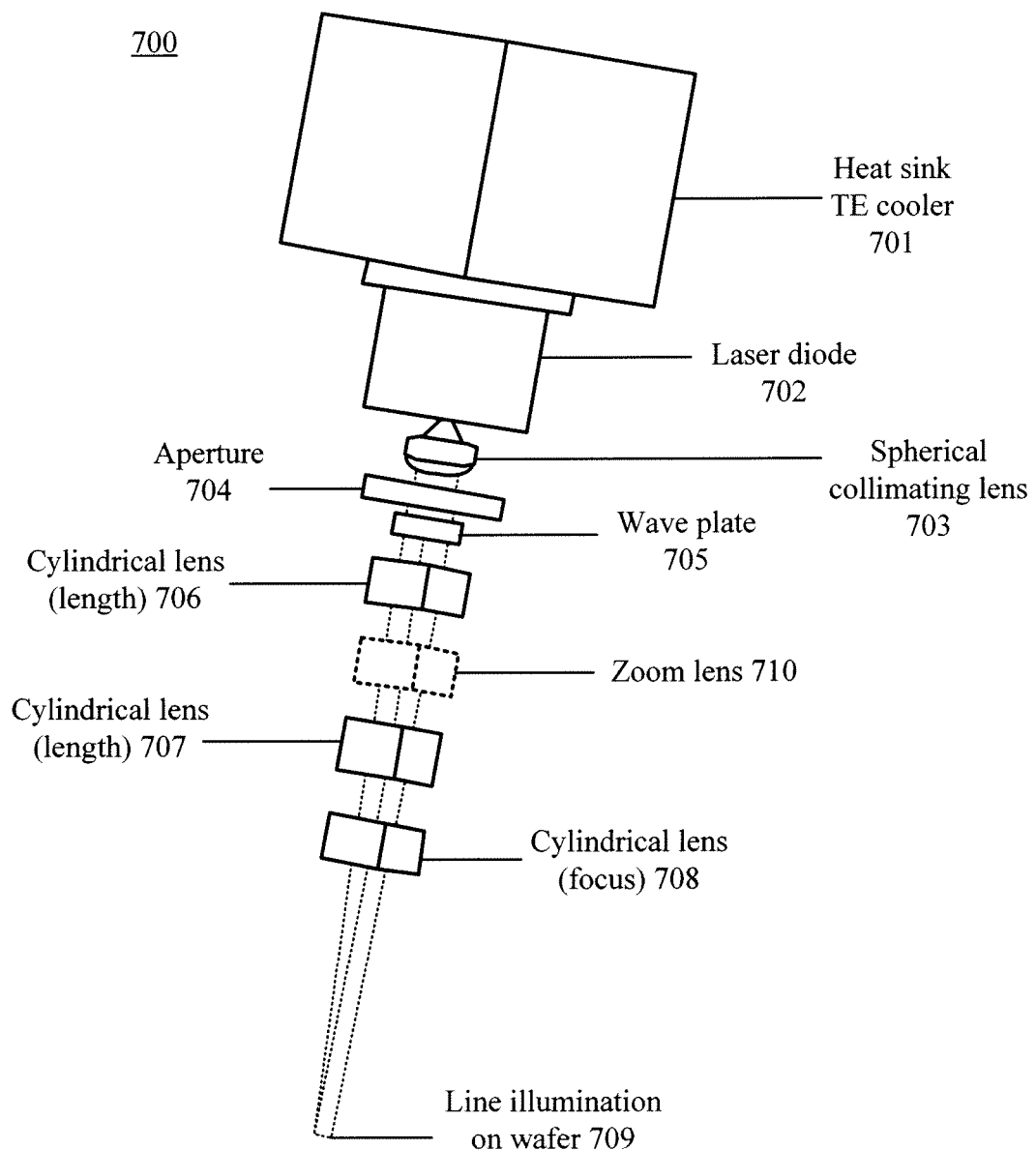
FIG. 7 illustrates an exemplary beam shaping path including three cylindrical lenses for providing multiple illuminated field lengths.

FIG. 7 illustrates an exemplary beam shaping path 700 including three cylindrical lenses for providing multiple illuminated line lengths. In this embodiment, beam shaping path 700 can include a laser diode 702, which can be cooled by a heat sink 701. In one embodiment, heat sink 701 can be implemented using a thermoelectric (TE) cooler and laser diode 702 can be implemented by a 9 mm diode. The light emitted by laser diode 702 can be collimated by a spherical collimating lens 703, and shaped by an aperture 704. The orientation of polarization is controlled by a wave plate 705. At this point, the light can be formed into a line 709 by at least two of cylindrical lenses 706, 707, and 708. In this embodiment, cylindrical lenses 706 and 707 can be used to determined line length, whereas cylindrical lens 708 can be used to focus the line (i.e. determine its width). In an actual implementation, a motor (not shown) can be used to exchange and move cylindrical lens 707, thereby providing a user with alternate line lengths for throughput and sensitivity adjustments. In another implementation, cylindrical lenses 706 and 707 can be replaced by a continuous zoom lens 710 that allows selection of a specific illumination line length within a predetermined range. Note that the above-described tilting and rotation refer only to cylindrical lens 708.

In one embodiment, each light source (see, e.g. FIG. 1A) has one corresponding beam shaping path 700. In other embodiments (discussed below), a single light source can generate a light beam, which is then divided into multiple light sources. Note that increasing the number of polar angles for the multiple light sources can advantageously increase the signal-to-noise ratio (SNR) (i.e. minimize the speckle) particularly above 2 angles.

Notably, there is a correspondence between the specific polar angles, the roughness of the wafer surface, and the speckle decrease. For example, for the relatively smooth wafer surface of a bare wafer, angles of 0 and 180 degrees for the light sources provide a smaller decrease in speckle compared to angles of 0 and 90 degrees. However, for a relatively rough wafer surface of a patterned wafer, either 90 or 180 degrees (with 0 degrees) can be used with comparable results. Thus, averaging for patterned wafers can be more effective than for unpatterned wafers with the same number of light sources. Note that a smaller SNR improvement may occur after 8 angles irrespective of wafer surface roughness because the increasing correlation between the speckle patterns generated by illuminations at smaller angular separation (wherein physically placing more than 8 light sources around a wafer may pose challenges in any case).

Note that particle detection sensitivity on a bare wafer is limited by the speckle noise of wafer surface roughness. For particle sizes that are much smaller than laser wavelength, the far field of scattered electric field for oblique P polarization (parallel to the plane of incidence) illumination is dominantly in P polarization for any specific scattering direction, and the intensity distribution has a donut shape. When the particle is imaged with high NA objective lens, the polarization is dominantly in the radial direction at the Fourier plane of the objective lens. Vector imaging simulation indicates that the dark field image of the particle under these conditions is not a Jinc function, which is the point spread function of the imaging lens predicated by scalar imaging theory. Notably, a captured image P-x (polarized in the x direction) added to a captured image P-y (polarized in the y direction) equal the capture image U, i.e. unpolarized. Therefore, in one embodiment, unpolarized images can be captured.

Figure 8:
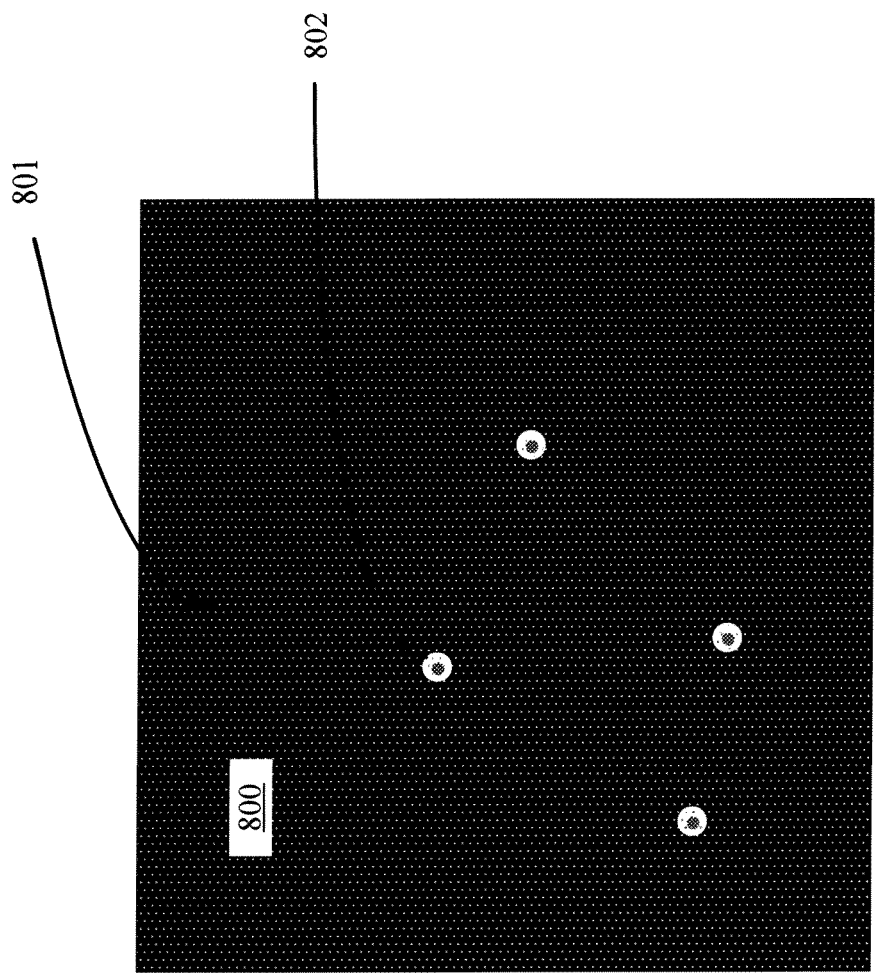
FIG. 8 illustrates an imaging sensor output representation of an unpatterned wafer surface including background speckle and four particles exhibiting a donut shaped image.

The captured image of a particle shows a dark center with a slightly asymmetrically weighed donut shape. FIG. 8 illustrates an imaging sensor output representation of a bare wafer surface 800 including background speckle 801 and four particles 802 exhibiting the donut shape. Notably, for multiple angles of illumination that are equally spaced in azimuth angle but similar in polar angle, the image of small particles for P polarization becomes a nearly perfect donut shape. As noted in FIG. 8, the unique signature of particles 802 can be clearly distinguished from speckle noise 801, thereby facilitating defect identification.

In one embodiment, a matched filter may be used in digital image processing (i.e. performed by the imaging sensor followed by a computer) to further reduce the speckle and thus improve SNR. For example, a simple digital image processing filter having the same shape as the particle image (donut shaped) can be used, while other types of filters may be used in other embodiments. Note that a matched filter is applicable to P polarization illumination, not S polarization illumination. Although P polarization illumination has much stronger scattering than S polarization illumination, P polarization can provide optimal sensitivity on wafers with low haze, such as polished Si (silicon) wafer and some smooth polysilicon wafers.

In one embodiment, the SNR can be further enhanced with a radial polarizer in the imaging path between the objective lens and the imaging sensor such that the polarization is aligned with the radial direction. This radial polarizer can reduce the speckle while passing most of the scattered light from small particles. Various combinations of illumination polarization and imaging polarization can be used for specific defect types. For example, the polarizations of illumination beams can be aligned to be in the same direction either parallel to x or y, and a linear polarizer can be used in collection path, either parallel to or perpendicular to the illumination polarization. These configurations can be advantageous for patterned wafer inspection where pattern features tend to be aligned with x and y directions. Notably, the separate lasers allow radial or tangential polarizations of illumination that otherwise would not be possible with a single point light source.

Numerous methods of delivering multiple laser beams to form a ring illumination, thereby making the multiple beams incoherent with respect to one another, can be provided. For example, in one embodiment, laser beams can be delivered via single-mode fiber from multiple lasers. Note that by using fibers as the light sources, these sources can be placed relatively far from the wafer, thereby providing system configuration flexibility where space is at a premium. In another embodiment, a beam from a single laser can be speckle treated first, thereby eliminating the coherence between the beams originated from the same laser, and then coupled into multiple fibers to illuminate wafer from multiple angles.

Figure 9:
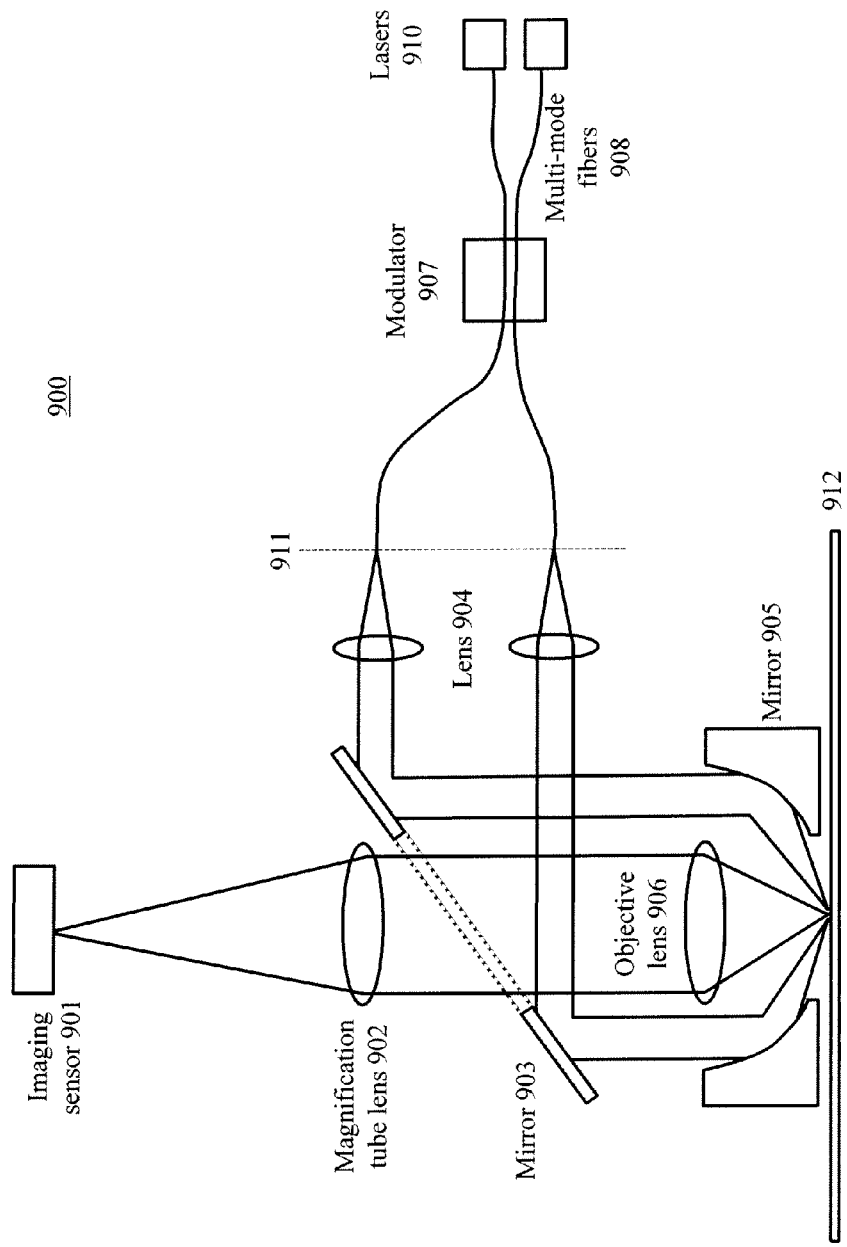
FIG. 9 illustrates an exemplary inspection system that can modulate (e.g. shake) the laser beams from multiple lasers, which are delivered via multi-mode fibers, to increase the averaging effect.

In an exemplary inspection system 900 shown in FIG. 9, a modulator 907 can modulate (e.g. shake) the fibers from multiple lasers 910, which are delivered via multi-mode fibers 908. This modulation can minimize speckle from laser sources using multimode interference. In this embodiment, lenses 904 can collimate and direct the light exiting at location 911 onto a mirror 903, which along with a parabolic mirror 905, can provide wide, large solid angles of light onto a wafer 912. Scattered light from wafer 912 can be gathered by an objective lens 906 (which has a large NA because it is reserved for imaging/collection only) and then focused by a magnification tube lens 902 onto an imaging sensor 901. In yet another embodiment, a beam from a single laser can be split into multiple beams and delivered via multi-mode fibers, wherein the multi-mode fibers can be modulated to minimize speckles.

Figure 10:
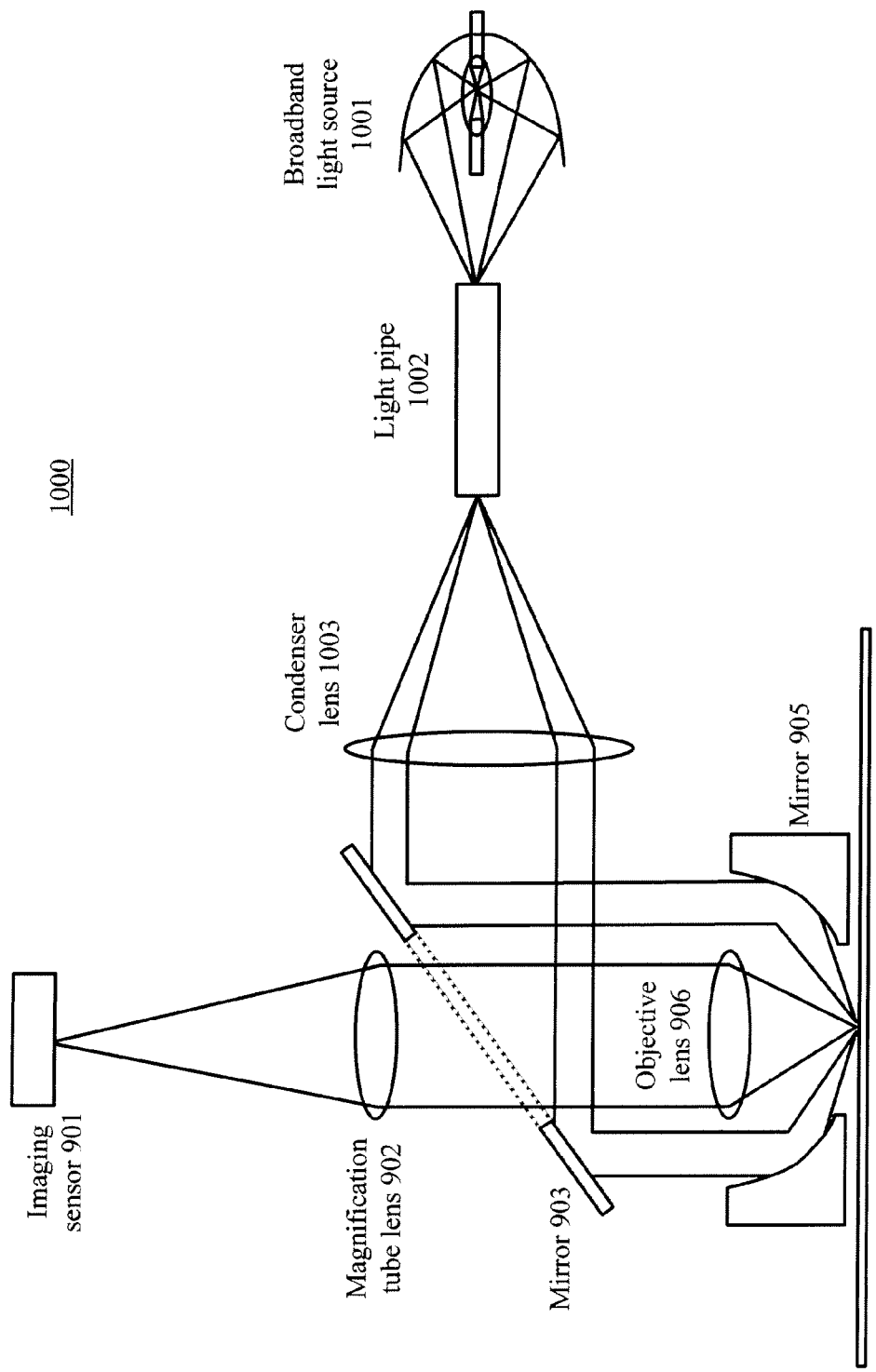
FIG. 10 illustrates an exemplary inspection system that can collimate light generated by a broadband light source to deliver it more efficiently to the final illumination mirror.

Note that light sources other than lasers or laser diodes can be used. For example, FIG. 10 illustrates an exemplary inspection system 1000 in which a light pipe 1002 can capture the light output by a broadband (incoherent) light source 1001. A condenser lens 1003 can collimate the incoherent, diverging light output by light pipe 1002 onto mirror 903 and the other components described in reference to FIG. 9 (wherein similar components are labeled the same). Therefore, this embodiment has the advantages described for FIG. 9 as well as the additional advantage of using different wavelengths, thereby further enhancing averaging.

Figure 11:
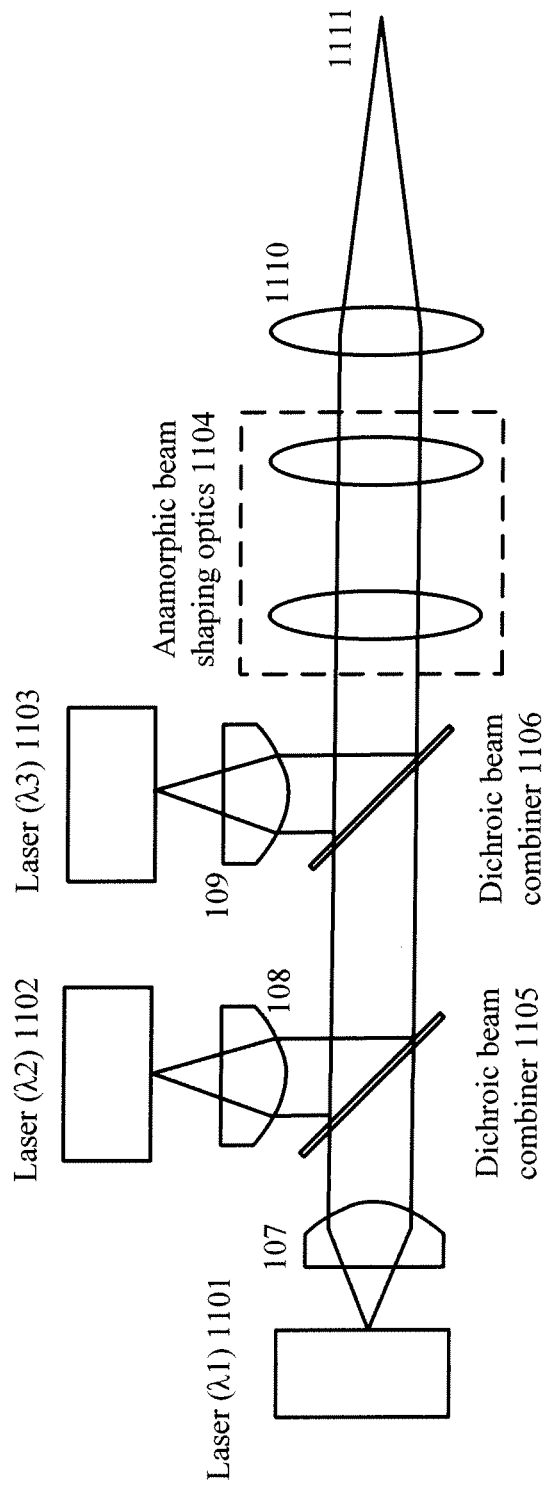
FIG. 11 illustrates combining laser beams of different wavelengths to increase the averaging effect and improve defect identification.

FIG. 11 illustrates combining laser beams of different wavelengths to increase the averaging effect. In one embodiment, light beams from lasers 1101, 1102, and 1103 (at wavelengths $\lambda 1$, $\lambda 2$, and $\lambda 3$, respectively) can be combined using dichronic beam combiners 1105 and 1106 (which reflect a first wavelength and pass a second wavelength). In this embodiment, lens 107, 108, and 109 collimate the laser beams prior to being combined. After combining, anamorphic beam shaping optics 1104 can introduce an unequal magnification along the perpendicular axes, of the combined beam, thereby changing its length or width independently.

Cylindrical lens 1110 forms a focused line onto wafer surface. Notably, certain wavelengths may be more effective than other wavelengths in detecting and identifying different defects on the wafer (e.g. particles). Therefore, using a beam comprising multiple wavelengths can improve the detection and identification of different types of defects on the wafer.

Figure 12:
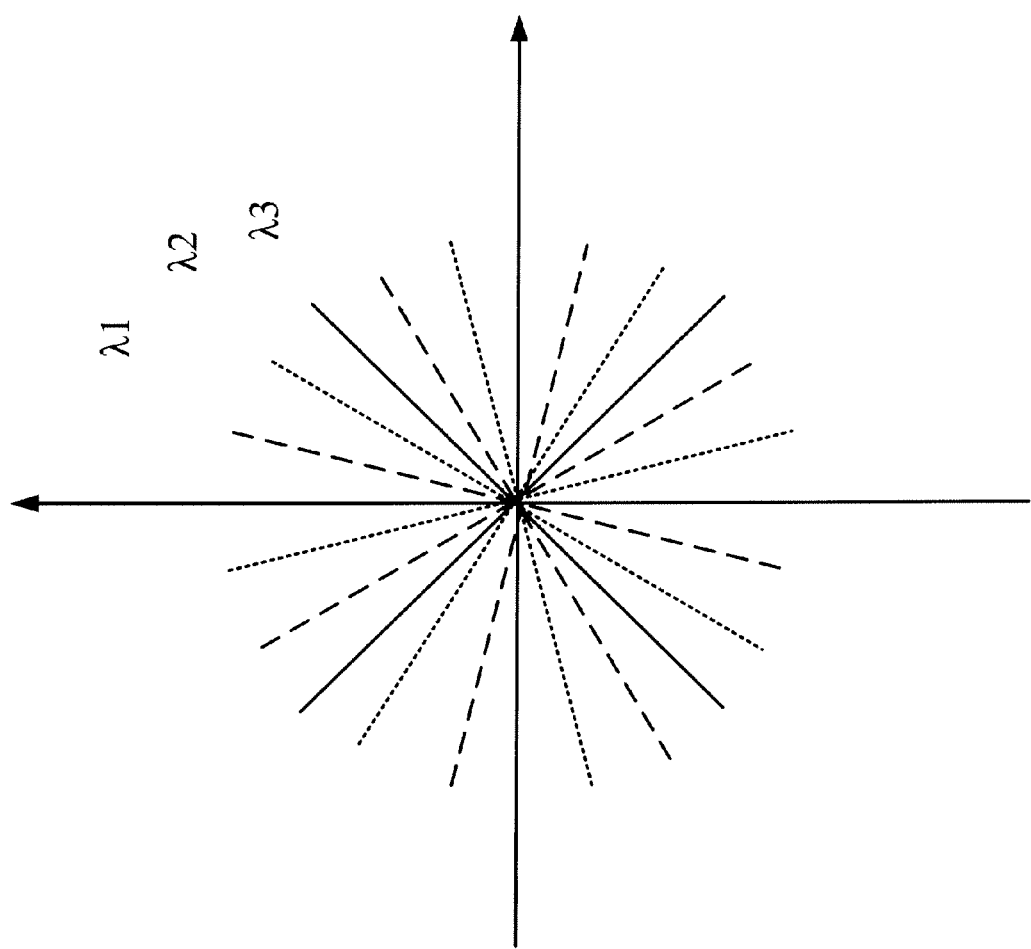
FIG. 12 illustrates using laser beams of different wavelengths interleaved at different polar angles to increase the averaging effect and improve defect identification.

FIG. 12 illustrates an embodiment in which the multiple light sources having three different wavelengths ($\lambda 1$, $\lambda 2$, and $\lambda 3$) can be interleaved. This interleaving may increase the system footprint compared to the embodiment shown in FIG. 11, but does provide an ability to track defect detection response for specific wavelengths. Note that, like the embodiment shown in FIG. 11, using laser beams of different wavelengths can increase the averaging effect and improve defect detection and identification.

Figure 13:
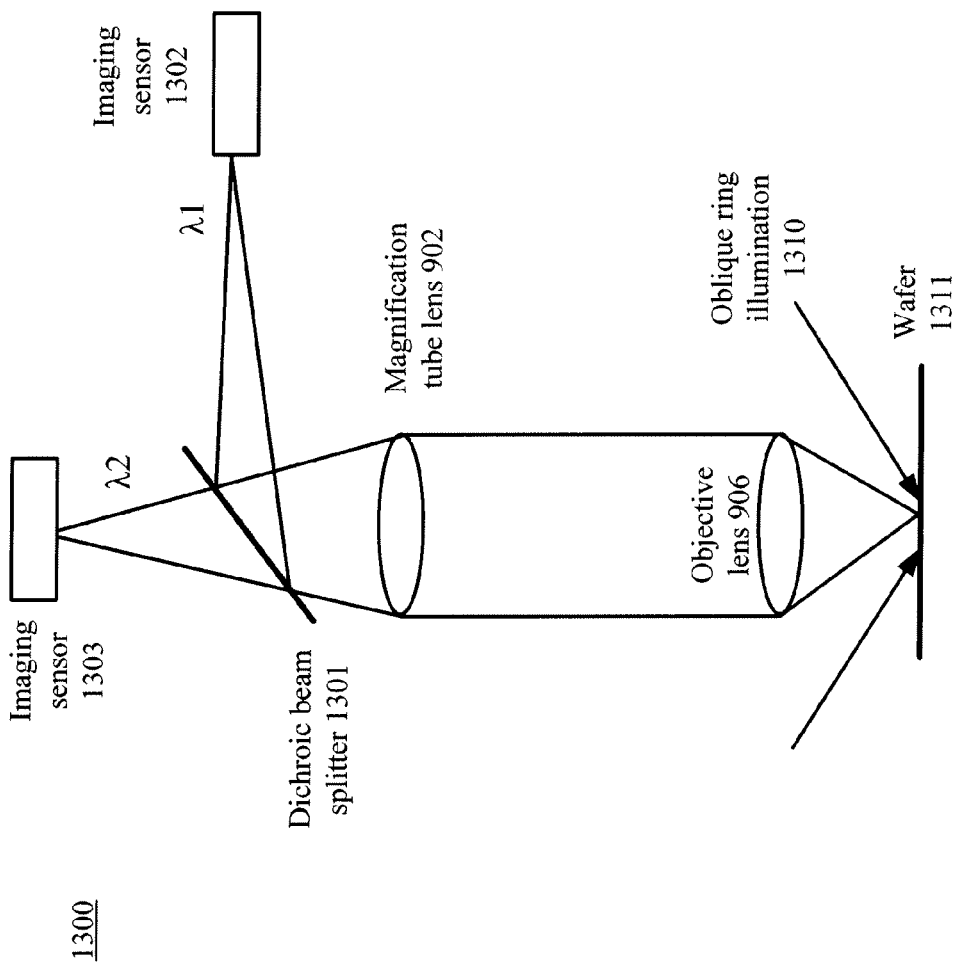
FIG. 13 illustrates an exemplary inspection system 1300 that includes multiple detection channels.

FIG. 13 illustrates an exemplary inspection system 1300 that includes multiple detection channels. In this embodiment, scattered light that results from an oblique ring illumination 1310 impinging wafer 1311 can be gathered by an objective lens 906 and then focused by a magnification tube lens 902 onto a first imaging sensor 1302 and a second imaging sensor 1303. Notably, a dichroic beam splitter 1301 can split the light based on wavelength and direct each wavelength to a specific imaging sensor. For example, wavelength $\lambda 1$ can be directed to imaging sensor 1302, whereas wavelength $\lambda 2$ can be directed to imaging sensor 1303. Note that in other embodiments another beam splitter can split the light based on three or more wavelengths and direct the light into three or more detection channels. In one embodiment using three wavelengths, the inspection system can select two detection channels. Notably, providing multiple detection channels based on different wavelengths can further enhance defect detection and classification.

Figure 14:
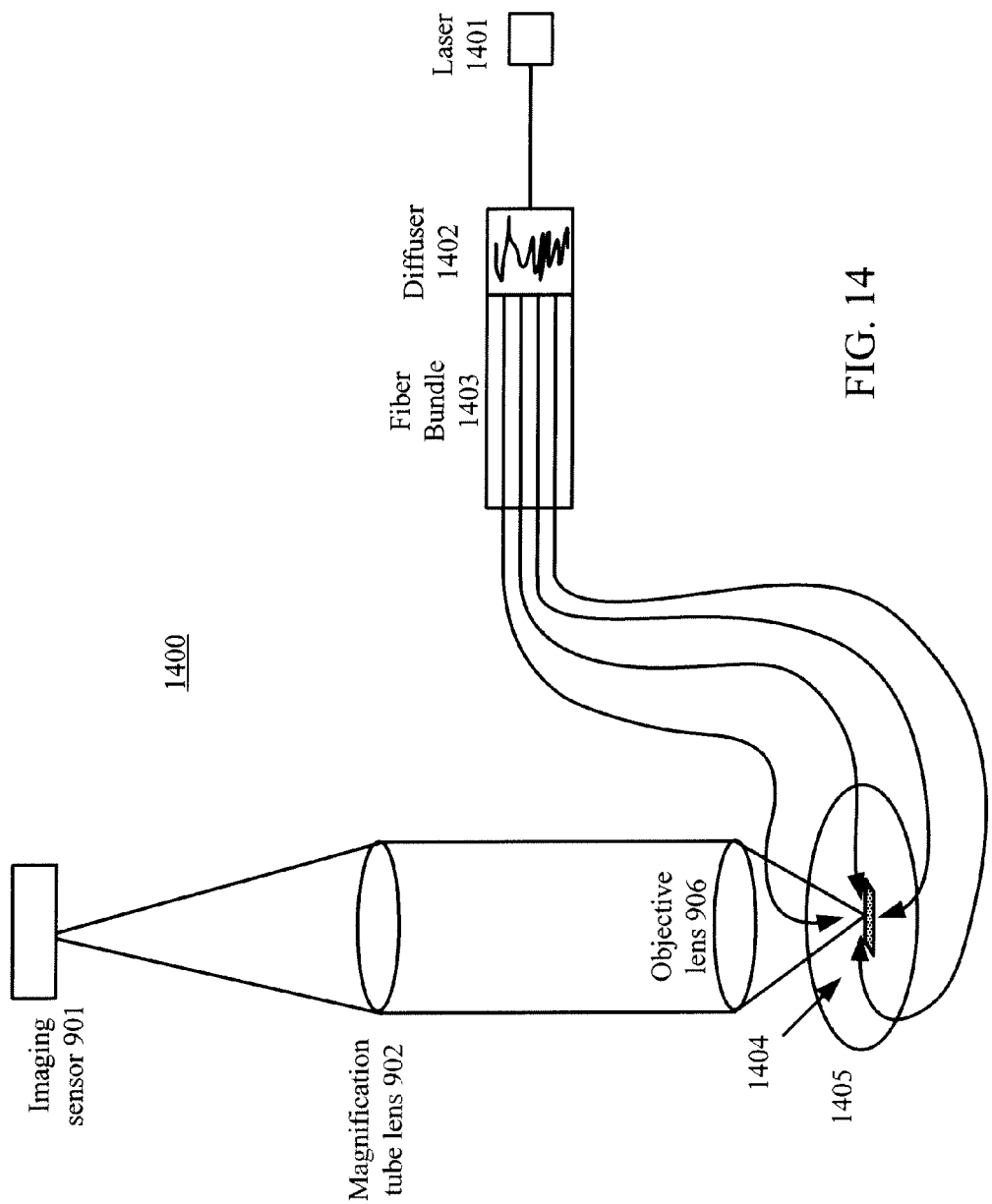
FIG. 14 illustrates an exemplary inspection system in which a diffuser can receive coherent light from a laser and generate incoherent light.

FIG. 14 illustrates an exemplary inspection system 1400 in which a diffuser 1402 can receive coherent light from a laser 1401 and generate incoherent light. This incoherent light can be captured by a fiber bundle 1403, wherein individual fibers can serve as light sources. Cylindrical lenses (not shown for simplicity) can be rotated and tilted as described above and then configured to provide ring illumination 1404. An imaging path including objective 906, magnification tube lens 902, and imaging sensor 901 can be used to capture the scattered light from wafer 1405. Note that the incoherent light can improve the averaging, thereby minimizing speckle.

The dark field inspection systems described above using ring illumination can provide high NA and minimize speckle, thereby resulting in improved resolution and sensitivity. The SNR of this system can be further enhanced by using a digital filter in image processing that matches the donut shape image of a particle. Light sources can include, but are not limited to, laser diodes, lasers, broadband light sources, super continuum light source, and multi-line lasers.

In the interest of clarity, not all features of an actual implementation are described above. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. For example, although embodiments including scanners are described herein, the present invention is equally applicable to steppers as well as any tools capable of modulating focus and exposure. All such modifications and variations are within the scope of the invention as determined by the appended claims when interpreted in accordance with the breadth to which they are fairly, legally, and equitably entitled.

The invention claimed is:

1. A dark field inspection system comprising:
three or more beam shaping paths for generating a composite, focused illumination line on a wafer, each beam shaping path for illuminating the wafer at an oblique angle, the beam shaping paths forming a ring illumination, wherein each of the beam shaping paths includes an independent light source positioned to result in independent, random noise at a surface of the wafer and wherein each independent light source provides incoherent light with respect to each other independent light source, wherein each of the plurality of beam shaping paths includes a cylindrical lens, each cylindrical lens being tilted and rotated with respect to a light beam from its corresponding light source, and wherein each cylindrical lens has a cylindrical axis positioned parallel to an illumination line, an optical axis, and a b-axis perpendicular to both the cylindrical axis and the optical axis, wherein the b-axis is positioned perpendicular to the light beam from its corresponding light source;
an objective lens for capturing scattered light from the wafer; and
an imaging sensor for receiving an output of the objective lens.

2. The dark field inspection system of claim 1, wherein the oblique angle with respect to the sample surface normal is between 60-85 degrees.

3. The dark field inspection system of claim 1, wherein a numerical aperture (NA) of the objective lens is at least 0.5.

4. The dark field inspection system of claim 1, wherein each cylindrical lens is rotated by its cylindrical axis to minimize aberration.

5. The dark field inspection system of claim 1, wherein at least one beam shaping path includes first, second, and third cylindrical lenses, wherein one of the first and second cylindrical lenses is in the beam shaping path at any point in time, wherein each of the first and second cylindrical lenses determines a length of the illumination line, and wherein the third cylindrical lens determines a width of the illumination line.

6. The dark field inspection system of claim 1, wherein at least one beam shaping path includes a continuous zoom lens and a cylindrical lens, wherein the continuous zoom lens allows selection of a specific illumination line length within a predetermined range, and wherein the cylindrical lens determines a width of the illumination line.

7. The dark field inspection system of claim 1, wherein the imaging sensor includes a digital image processing filter that matches a shape of a particle on the wafer.

8. The dark field inspection system of claim 7, wherein the shape is a donut shape.

9. The dark field inspection system of claim 1, wherein each light source is a laser.

10. The dark field inspection system of claim 1, wherein the three or more beam shaping paths include:
- multiple lasers;
- multi-mode fibers coupled to the multiple lasers;
- a modulator for modulating beams carried by the multi-mode fibers; and
- mirrors for reflecting and directing the beams for generating the illumination line.

11. The dark field inspection system of claim 10, wherein the mirrors include an aspheric ring mirror.

12. The dark field inspection system of claim 1, wherein the three or more beam shaping paths include:
- a broadband light source;
- a light pipe receiving an output of the broadband light source;
- a condenser lens for collimating output of the light pipe; and
- mirrors for reflecting and directing beams output from the condenser lens for generating the illumination line.

13. The dark field inspection system of claim 12, wherein the mirrors include an aspheric ring mirror.

14. The dark field inspection system of claim 1, wherein at least one light source includes multiple lasers and dichroic beam combiners for generating a laser beam having multiple wavelengths.

15. The dark field inspection system of claim 1, wherein each light source is a laser, and adjacent beam shaping paths have lasers with different wavelengths.

16. The dark field inspection system of claim 1, wherein the three or more beam shaping paths include:
- a laser;
- a diffuser coupled to the laser; and
- a fiber bundle for receiving an output of the diffuser,
- wherein each fiber contributes light to form the illumination line.

17. The dark field inspection system of claim 1, wherein each light source is a laser diode.

18. The dark field inspection system of claim 1, further including a beam splitter positioned to receive an output of the objective lens, wherein the imaging sensor includes a first imaging sensor for detecting a first wavelength of light output by the beam splitter and a second imaging sensor for detecting a second wavelength of light output by the beam splitter.

19. The dark field inspection system of claim 1, further including a beam splitter positioned to receive an output of the objective lens, wherein the imaging sensor includes multiple imaging sensors, each imaging sensor for detecting a specific wavelength of light output by the beam splitter.

20. The dark field inspection system of claim 19, wherein a subset of the multiple imaging sensors is selected for image analysis.

21. A method of providing a dark field inspection system, the method comprising:
- forming three or more beam shaping paths to provide ring illumination, each beam shaping path for illuminating a wafer at an oblique angle, wherein outputs of the three or more beam shaping paths form a focused illumination line on the wafer, wherein each of the plurality of beam shaping paths includes an independent light source positioned to result in independent, random noise at a surface of the wafer, wherein each independent light source provides incoherent light with respect to each other independent light source, and wherein forming the three or more beam shaping paths includes tilting and rotating at least one cylindrical lens in each beam shaping path, wherein each cylindrical lens has a cylindrical axis positioned parallel to the illumination line, an optical axis, and a b-axis perpendicular to both the cylindrical axis and the optical axis, wherein the b-axis is positioned perpendicular to the light beam from its corresponding light source.

22. The method of claim 21, further including rotating at least one cylindrical lens by its cylindrical axis to minimize aberration.

23. The method of claim 21, further including using a first cylindrical lens to determine a length of the illumination line and a second cylindrical lens to determine a width of the illumination line.

24. The method of claim 21, further including using a zoom lens to determine a length of the illumination line and a cylindrical lens to determine a width of the illumination line.

25. The method of claim 21, wherein forming the three or more beam shaping paths includes:
- coupling multi-mode fibers to outputs of coherent light sources;
- modulating beams carried by the multi-mode fibers; and
- reflecting and directing modulated beams for generating the illumination line.

26. The method of claim 21, wherein forming the three or more beam shaping paths includes:
- coupling a light pipe to an output of an incoherent light source;
- collimating outputs of the light pipe; and
- reflecting and directing beams collimated outputs for generating the illumination line.

27. The method of claim 21, wherein forming the three or more beam shaping paths includes:
- in at least one beam shaping path, combining outputs from a plurality of lasers, each laser having a different wavelength.

28. The method of claim 21, wherein forming the three or more beam shaping paths includes:
- providing lasers with different wavelengths in adjacent beam shaping paths.

29. The method of claim 21, wherein forming the three or more beam shaping paths includes:
- coupling a diffuser to an output of a laser; and
- coupling a fiber bundle to outputs of the diffuser,
- wherein each fiber of the fiber bundle contributes light to form the illumination line.

30. The method of claim 21, wherein the oblique angle is between 60-85 degrees with respect to the sample surface normal.

* * * * *